(12) United States Patent  (10) Patent No.: US 7,621,106 B2
Tackett et al.  (45) Date of Patent: Nov. 24, 2009

(54) TAMPON WRAPPER

(75) Inventors: Douglas L. Tackett, Dover, DE (US); Robert Jorgensen, Middletown, DE (US); Keith Edgett, Middletown, DE (US); Peter Preisner, Quinton, VA (US); Wojtek Drewnowski, Richmond, VA (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 11/888,973

(22) Filed: Aug. 3, 2007

(65) Prior Publication Data

US 2008/0058749 A1 Mar. 6, 2008

Related U.S. Application Data

(60) Provisional application No. 60/835,637, filed on Aug. 4, 2006.

(51) Int. Cl.
*B65B 61/18* (2006.01)

(52) U.S. Cl. .................. 53/412; 53/133.8; 53/563; 206/440

(58) Field of Classification Search ........... 206/440, 206/484; 53/412, 133.8, 459, 563; 604/385.02; 229/87.01, 87.05; 383/200, 203, 207
See application file for complete search history.

(56) References Cited

U.S. PATENT DOCUMENTS

| | | | | |
|---|---|---|---|---|
| 2,106,748 A | | 2/1938 | Karnes et al. ............ 229/87.05 |
| D138,697 S | * | 9/1944 | Salfisberg .................... D9/707 |
| 3,092,251 A | * | 6/1963 | Jaggers ....................... 206/446 |
| 3,276,670 A | * | 10/1966 | Harvey .......................... 383/77 |
| 3,291,377 A | | 12/1966 | Eggen ......................... 426/122 |
| 3,480,198 A | * | 11/1969 | Repko .......................... 383/203 |
| 3,566,752 A | | 3/1971 | Dreher ......................... 493/197 |
| 3,625,351 A | * | 12/1971 | Eisenberg .................... 206/484 |
| 3,809,217 A | * | 5/1974 | Harrison ....................... 206/84 |
| 4,212,301 A | | 7/1980 | Johnson |
| 4,218,863 A | | 8/1980 | Howard et al. |
| 4,421,823 A | * | 12/1983 | Theisen et al. .............. 428/349 |
| 4,504,434 A | * | 3/1985 | Cooper ........................ 264/222 |
| 4,648,513 A | * | 3/1987 | Newman ..................... 383/204 |
| 4,881,644 A | * | 11/1989 | Norquest et al. ............ 206/363 |
| 4,973,302 A | | 11/1990 | Armour et al. |
| 5,084,038 A | | 1/1992 | Sheldon et al. |
| 5,133,457 A | * | 7/1992 | Kadel .......................... 206/438 |
| 5,407,611 A | * | 4/1995 | Wilhoit et al. .............. 264/483 |
| 5,442,897 A | * | 8/1995 | Hinzmann et al. ............. 53/449 |
| 5,445,454 A | * | 8/1995 | Barkhorn .................... 383/207 |
| 5,489,060 A | | 2/1996 | Godard .................... 229/87.05 |

(Continued)

FOREIGN PATENT DOCUMENTS

DE  4115000  12/1991

(Continued)

OTHER PUBLICATIONS

International Search Report based on PCT/US07/17486, dated Sep. 8, 2008.

(Continued)

*Primary Examiner*—David T Fidei
(74) *Attorney, Agent, or Firm*—Ohlandt, Greeley, Ruggiero & Perle, L.L.P.

(57) ABSTRACT

The present disclosure provides a tampon wrapper that is a polyethylene film tube having at least a first sealed end with a notch in the first sealed end, and a number of perforations extending from the notch along the axial length of the tampon wrapper. The wrapper is quiet, easy to open, and provides a sanitary method of storing a used applicator.

7 Claims, 6 Drawing Sheets

U.S. PATENT DOCUMENTS

| | | | | |
|---|---|---|---|---|
| 5,520,764 | A * | 5/1996 | Toney et al. | 156/244.17 |
| 5,698,217 | A * | 12/1997 | Wilking | 424/448 |
| 5,719,206 | A * | 2/1998 | Mihoya et al. | 523/212 |
| 5,964,741 | A | 10/1999 | Moder et al. | |
| 5,986,165 | A | 11/1999 | Moder et al. | |
| 6,110,092 | A | 8/2000 | Focke et al. | 493/375 |
| 6,131,374 | A | 10/2000 | Bois | |
| 6,140,386 | A * | 10/2000 | Vanderhoff et al. | 522/78 |
| 6,342,258 | B1 | 1/2002 | Berings et al. | 426/79 |
| 6,352,364 | B1 | 3/2002 | Mobs | 383/200 |
| 6,478,763 | B1 * | 11/2002 | Simonsen et al. | 602/79 |
| 6,955,665 | B2 * | 10/2005 | Domeier et al. | 604/385.02 |
| 7,101,358 | B2 | 9/2006 | Domeier et al. | 604/385.02 |
| 7,422,105 | B2 | 9/2008 | Lyod et al. | 206/438 |
| 7,434,371 | B2 | 10/2008 | Stivani et al. | 53/412 |
| 2003/0029740 | A1 * | 2/2003 | Caveness | 206/210 |
| 2003/0065300 | A1 * | 4/2003 | Suga | 604/385.02 |
| 2003/0233813 | A1 * | 12/2003 | Leslie et al. | 53/412 |
| 2004/0112779 | A1 * | 6/2004 | Arndt | 206/363 |
| 2005/0092642 | A1 * | 5/2005 | Nyambi | 206/440 |
| 2005/0094903 | A1 * | 5/2005 | Nyambi | 383/116 |
| 2006/0048484 | A1 * | 3/2006 | Wasson et al. | 53/450 |
| 2006/0113361 | A1 | 6/2006 | Aeschlimann et al. | 229/87.05 |
| 2008/0135428 | A1 | 6/2008 | Tallier | 206/264 |

FOREIGN PATENT DOCUMENTS

| | | |
|---|---|---|
| DE | 4041743 | 6/1992 |
| EP | 229907 | 7/1987 |
| FR | 2836826 | 9/2003 |

OTHER PUBLICATIONS

Written Opinion based on PCT/US07/17486, dated Sep. 8, 2008.

* cited by examiner

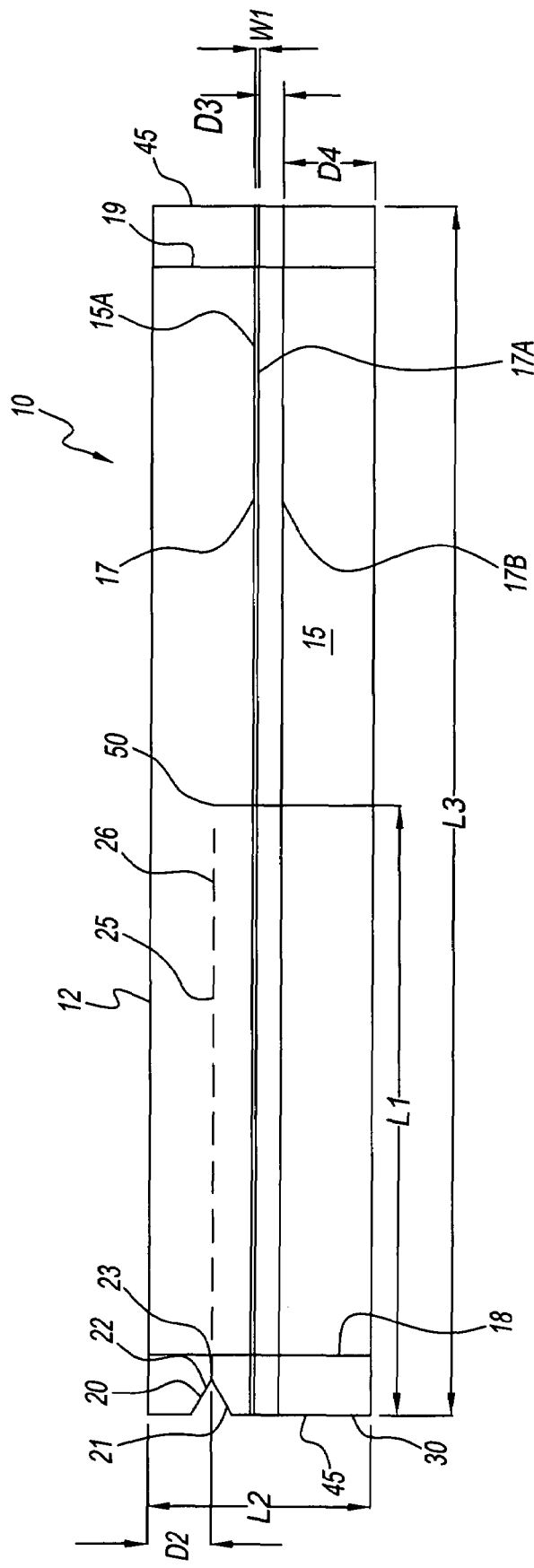

TAMPON WRAPPER

CROSS REFERENCE TO RELATED PATENT APPLICATIONS

This application claims the benefit of U.S. Provisional Application Ser. No. 60/835,637 filed Aug. 4, 2006 entitled "Tampon Wrapper," now pending. The aforementioned application is hereby incorporated herein by reference in its entirety.

BACKGROUND OF THE INVENTION

1. Field of the Invention

The present disclosure is related to tampon wrappers. More particularly, the present disclosure is related to a polyethylene tampon wrapper.

2. Description of the Related Art

Tampons are typically made commercially available with protective wrappers. Wrappers provide protection of the tampon from being soiled prior to use. To use the tampon, the wrapper is opened, the tampon is removed from the wrapper and inserted into the body. If the tampon has an applicator, the applicator will contact fluids from the user's body during insertion. The user must undesirably handle the used applicator prior to disposal after insertion. The wrapper and applicator are generally discarded separately.

Tampon wrappers made of polypropylene that are currently available to consumers produce noise or sound upon a user tearing the wrapper to access the tampon. The noise may be heard by others, and, thus, does not allow the user to be discreet while using a tampon. However, materials other than polypropylene can be undesirably difficult to open.

Accordingly, there is a need for an improved tampon wrapper that is quieter and more discreet than conventional wrappers by reducing noise during tampon removal from the wrapper and that provides an opening mechanism that allows a user easy access to the tampon therein. There is a further need for a sanitary method of storage of a used applicator and plunger after insertion of a tampon pledget. The present disclosure meets these needs.

SUMMARY OF THE INVENTION

The present disclosure provides a polyethylene tampon wrapper.

The present disclosure also provides such a tampon wrapper that provides a method of easily locating an end of a tampon applicator in the tampon wrapper to consistently open the tampon wrapper at a plunger end and avoid contact with a barrel.

The present disclosure further provides such a tampon wrapper that has a notch that provides a lead-in to a perforation so that a user can easily tear the tampon wrapper along the perforation.

The present disclosure still further provides such a tampon wrapper that has a natural stopping mechanism that is formed by a portion on the polyethylene of the tampon wrapper making it more difficult to tear the wrapper other than along the perforation due to a resistance of the polyethylene of the tampon wrapper.

The present disclosure yet further provides the perforation to allow the user consistent tearing of the tampon wrapper.

The present disclosure also provides such a tampon wrapper that after tearing the tampon wrapper along the perforation has two exposed ends that allows the user a sanitary method of storage of a used applicator and plunger. This structure provides an option of tying the two exposed ends together for disposal at a time that is more convenient to the user.

These and other advantages of the present disclosure are provided by a tampon wrapper including a polyethylene film tube having at least a first sealed end and a notch in the first sealed end.

The above-described and other features and advantages of the present disclosure will be appreciated and understood by those skilled in the art from the following detailed description and drawings.

BRIEF DESCRIPTION OF THE DRAWINGS

FIG. 1 is a side view of an exemplary embodiment of a tampon wrapper of the present disclosure;

DETAILED DESCRIPTION OF THE INVENTION

Figure 1A:
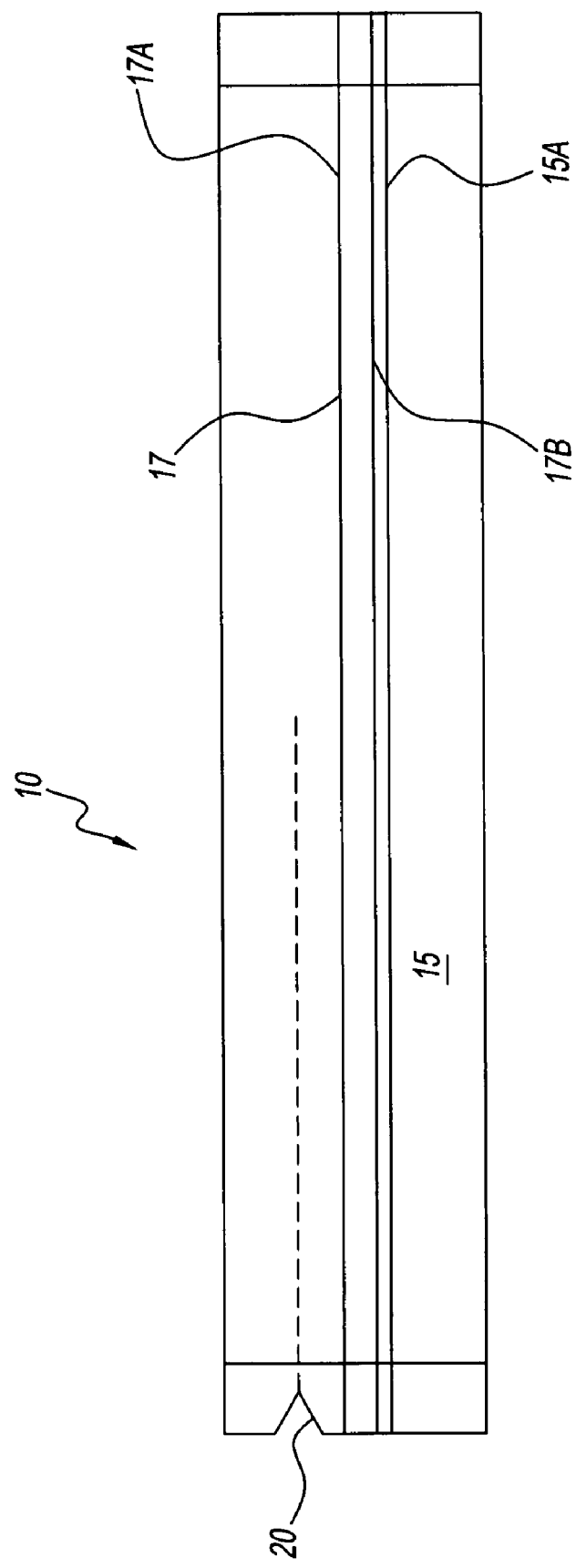
FIG. 1A is a side view of the tampon wrapper of FIG. 1 with an end portion of a polyethylene film that extends beyond a bottom portion of a longitudinal seal.

Referring to the figures and, in particular, to FIG. 1, a first exemplary embodiment of a tampon wrapper of the present disclosure is generally represented by reference numeral 10. The tampon wrapper 10 is made of a polyethylene film material. Preferably, tampon wrapper 10 is made of a polyethylene film material in the shape of a tube 15. Significantly, the tampon wrapper 10 has a notch 20.

Figure 2:
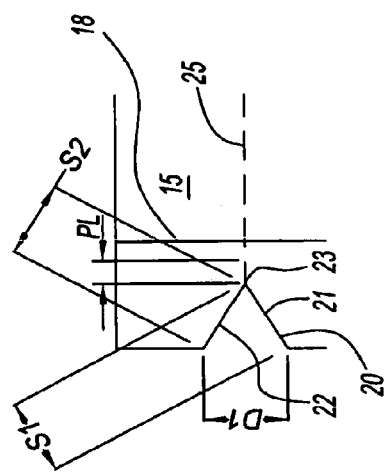
FIG. 2 is an enlarged partial side view of the tampon wrapper of FIG. 1.

Referring to a first exemplary embodiment in FIGS. 1 through 4, notch 20 is an indentation, such as, for example, a triangular indentation, on tampon wrapper 10. Preferably, the notch 20 is an equilateral triangular indentation, as shown in FIG. 2, with a first side or wall 21 having a first length S1 and a second side or wall 22 having a second length S2 and a maximum distance D1 between first and second walls 21 and 22. However, notch 20 may have any shape, such as, for example, rectangular or curved.

In one embodiment of the present disclosure, the first length S1, second length S2, and maximum distance D1 may each be about 0.095 inches to about 0.345 inches, and, preferably, are about 0.22 inches. Referring to FIGS. 1 and 2, notch 20 may be formed by two indentations that are on an outer perimeter at a first end 30 of tube 15 so that the indentations match up on an overlapping portion of polyethylene film of tube 15 when rolled over. The notch 20 will allow the user to easily identify the proper end of the tampon wrapper 10 to be opened. Preferably, notch 20 identifies the end of the tampon wrapper 10 that upon opening tampon wrapper 10 exposes the plunger end in order for the user to avoid contact with the applicator barrel.

Referring to FIGS. 1 and 2, a second exemplary embodiment of the tampon wrapper 10 of the present disclosure has notch 20 and also one or more, and preferably two or more, perforations 25. The perforations 25 are one or more, and preferably two or more, openings or slits through tampon wrapper 10. Preferably, perforations 25 begin at a point 23 where first wall 21 and second wall 22 of notch 20 meet. The perforations 25 are formed longitudinally along tube 15 beginning at point 23 and extending along a perforation length L1 of tampon wrapper 10. The perforation length L1 may be about 3.075 inches to about 3.325 inches, and, preferably, is about 3.2 inches. The perforations 25 may have a perforation distance D2 from a longitudinal side edge 12 of tampon wrapper 10. The perforation distance D2 may be about 0.20 inches to about 0.452 inches, and, more preferably, about 0.327 inches.

In this embodiment, notch 20 provides a lead-in to perforations 25 so that the user can easily tear tampon wrapper 10 along perforations 25. A natural stopping mechanism 50 is formed by a portion on tube 15 after a last perforation 26 of perforations 25, making it more difficult to tear tampon wrapper 10 other than along perforations 25 due to a resistance of the polyethylene material. The perforations 25 allow the user consistent tearing of tampon wrapper 10. Each perforation 25 may have a perforation length PL of up to about 0.1875 inches, and, more preferably, about 0.0625 inches. The perforations 25 may be in a perforation pattern that has about 0.109 (7/64) inch cuts in the longitudinal direction with about 0.063 (1/16) inch landings in the longitudinal direction. The cuts are severed portions of perforations 25 where a cutting mechanism has placed a slit in the polyethylene film and landings are portions of perforations 25 where the polyethylene film is uncut.

Figure 3:
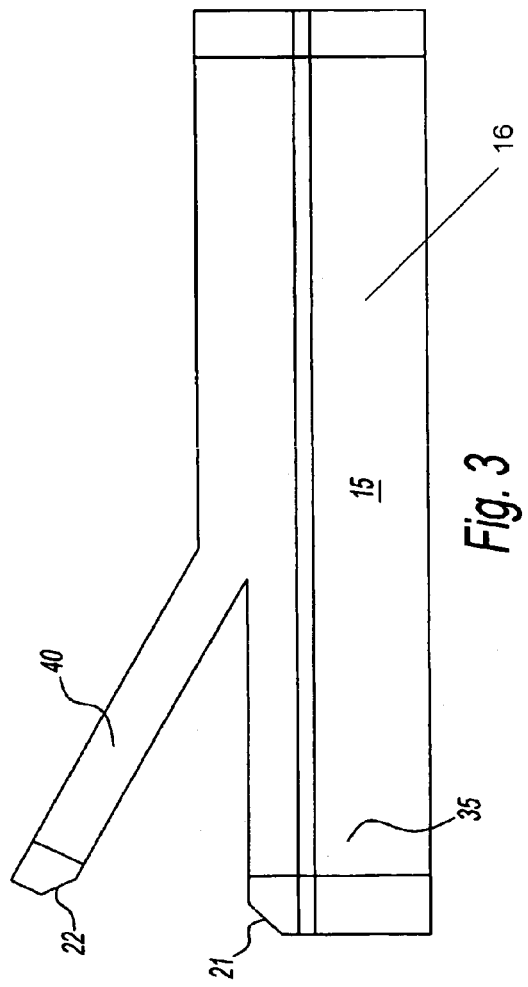
FIG. 3 is a side view of the tampon wrapper of FIG. 1 that is split into a first portion and a second portion.
Figure 4:
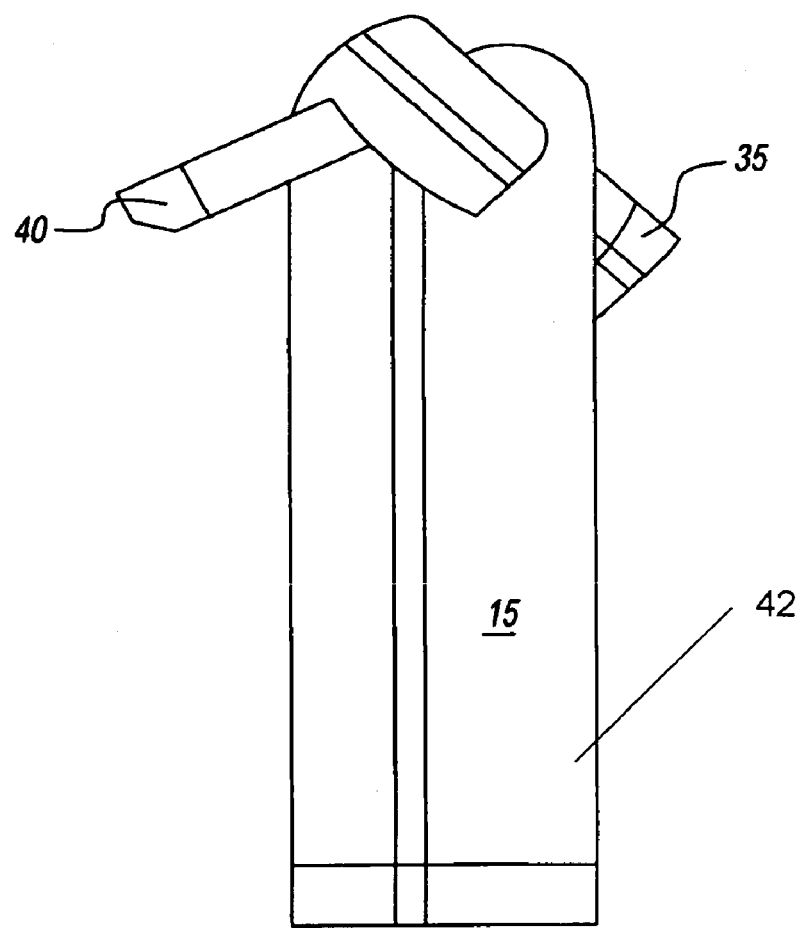
FIG. 4 is side view of the tampon wrapper of FIG. 1 with the first portion and second portion tied.

Referring to FIGS. 3 and 4, the user may tear tampon wrapper 10 along perforations 25 to split tampon wrapper into an open volume portion 16, a first portion 35 and a second portion 40 to open tampon wrapper 10. Thus, perforations 25 and polyethylene material of tube 15 allow the user to open tampon wrapper 10 easily and with reduced noise over the prior art tampon wrappers, such as tampon wrappers made of polypropylene material.

In another aspect of the present disclosure, the first portion 35 and second portion 40 may be tied to form a closed volume 42, thereby facilitating disposal of a used tampon applicator and/or applicator plunger. After splitting tampon wrapper 10 into first portion 35 and second portion 40, the user may place a used tampon applicator and/or applicator plunger into open volume portion 16 of tampon wrapper 10 and tie first portion 35 and second portion 40 to form closed volume 42 with the used tampon applicator and/or applicator plunger therein. Thus, the user is provided with a sanitary method of storage of the used tampon applicator and/or applicator plunger in closed volume 42 of tampon wrapper 10 allowing the user to dispose of tampon wrapper 10 and the used tampon applicator and/or applicator plunger as desired, such as at a time that is more convenient.

Referring again to FIG. 1, tube 15 may have a longitudinal seal 17. The tube 15 may be sealed on first end seal 18 and second end seal 19. The longitudinal seal 17, first end seal 18, and second end seal 19 form an interior volume that can house a tampon pledget and/or tampon applicator. The first end seal 18 and second end seal 19, preferably, are about 0.30 inches to about 0.44 inches, and more preferably, about 0.3125 inches from outer edges 45 of tube 15. The first end seal 18 and second end seal 19 may have a length L2 of about 1.062 inches to about 1.380 inches, and more preferably, about 1.1875 inches or about 1.25 inches. The longitudinal seal 17 may have a length L3 of about 6.17 inches to about 6.43 inches, and more preferably, about 6.3 inches. The longitudinal seal 17 extends from a top edge 17A to a bottom edge 17B. A distance D3 from top edge 17A to bottom edge 17B may be, such as, for example, up to about 0.25 inches, and more preferably, about 0.125 inches. The longitudinal seal 17, preferably, is a side distance D4 of about 0.37 inches to about 0.69 inches, and more preferably, about 0.5 inches to about 0.5625 inches from each edge of first and second end seals 18 and 19. An end portion 15A of the polyethylene film of tube 15 may extend beyond top edge 17A forming a flap. The end portion 15A may have a width W1 that may be up to about 0.141 inches, and more preferably, about 0.01563 inches. Alternatively, end portion 15A may extend beyond bottom edge 17B of longitudinal seal 17, as shown in FIG. 1A.

The polyethylene of tampon wrapper 10, preferably, is a low density polyethylene film that is corona treated on either one side or both sides. The polyethylene film may be about 40 microns in thickness. The polyethylene film may be embossed with a Huhtamaki Atlas 3 embossing. Huhtamaki Atlas 3 embossing may emboss film with raised and recessed impressions created by an embossing or debossing component. The polyethylene film can be any color, such as, for example, Pantone 376c (green), Pantone 7485C (light green), PMS 129C (yellow), or Pantone 263C (violet). Pantone is a corporation that markets and sells Pantone matching systems (PMS) for matching colors used in printing and the manufacture of inks, paints, fabrics and plastics. The polyethylene film can be printed in PMS 123C (golden yellow), PMS 205C (pink), PMS 361C (lime green), PMS 190C (light pink), PMS 358C (green), or PMS 151C (orange) colored ink.

Preferably, a method of making the tampon wrapper 10 includes perforating a polyethylene film while in flat state. The polyethylene film is rolled over to form a tube in preparation for knurling and/or heat sealing. Knurling and/or heat sealing the polyethylene film forms longitudinal seal 17 along a length of the tampon wrapper 10. A first perforated end-seal or end-seal side is formed by knurling and/or heat sealing the polyethylene film. A notch 20 is punched out of the perforated end-seal of the tampon wrapper 10. A tampon pledget and/or tampon applicator is inserted into the polyethylene film that has the sealed first perforated end-seal. A second end-seal is formed by knurling and/or heat sealing the polyethylene film thereby sealing the pledget and/or tampon applicator inside of the tampon wrapper 10. The longitudinal seal 17 is knurled at a temperature of about 80 degrees Celsius to 120 degrees Celsius. The end seals are knurled at a temperature of about 80 degrees Celsius to 120 degrees Celsius. The polyethylene film may have a melting point of 120 degrees Celsius.

An alternative method of making the tampon wrapper may include notching and perforating the polyethylene film while in flat state. The polyethylene film may be rolled over in preparation for knurling and/or heat sealing. Knurling and/or heat sealing the polyethylene film forms a longitudinal seal along a length of the tampon wrapper. A notch end-seal or end-seal side is formed by knurling and/or heat sealing the polyethylene film. A tampon pledget and/or tampon applicator is inserted into the polyethylene film that has the sealed notch end-seal. A final end-seal is formed by knurling and/or heat sealing the polyethylene film sealing the pledget and/or tampon applicator inside of the tampon wrapper 10. The longitudinal seal is knurled at a temperature of about 80 degrees Celsius to 120 degrees Celsius. The end seals is knurled at a temperature of about 80 degrees Celsius to 120 degrees Celsius. The polyethylene film may have a melting point of 120 degrees Celsius.

Figure 5:
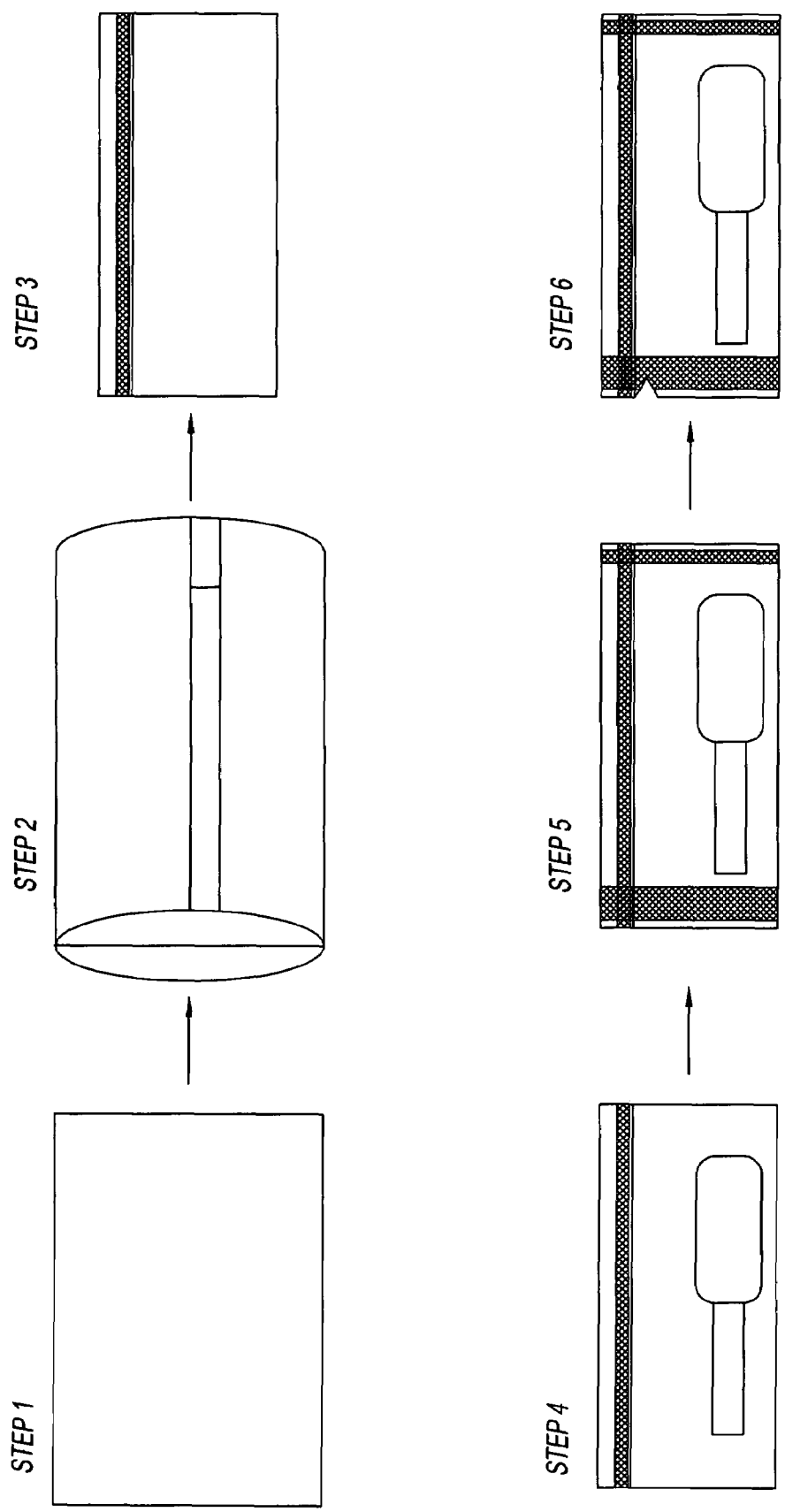
FIG. 5 is a schematic diagram of a method of making the tampon wrapper of the present disclosure.
Figure 7:
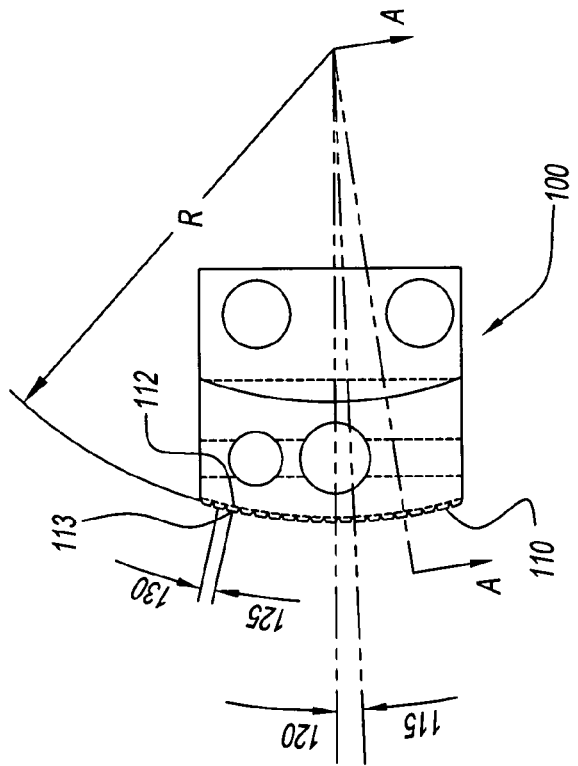
FIG. 7 is a schematic diagram of a side view of the end seal knurl pattern of FIG. 6.
Figure 9:
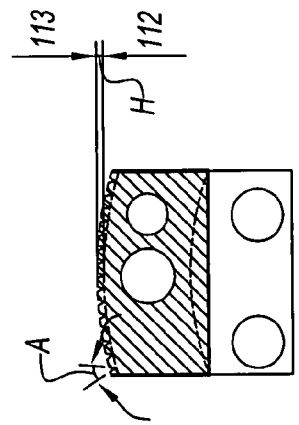
FIG. 9 is a cross-sectional view along B-B of the end seal knurl pattern of FIG. 6.
Figure 6:
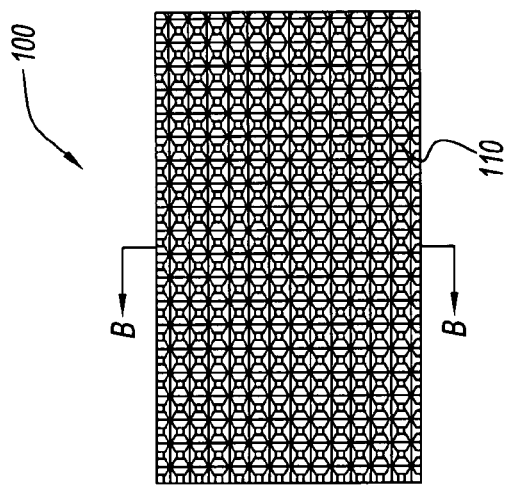
FIG. 6 is a schematic diagram of a top view of an exemplary end seal knurl pattern.
Figure 8:
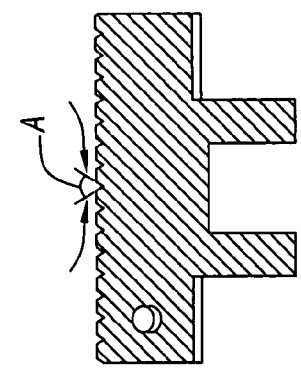
FIG. 8 is a cross-sectional view along A-A of the end seal knurl pattern of FIG. 7.

Another alternative method of making the tampon wrapper 10 is shown in FIG. 5. The method includes step 1, namely providing a polyethylene film while in flat state. Step 1 also includes an unwind direction shown by arrow A. The unwind direction is the direction that the polyethylene film unwinds from a roll of polyethylene film. In Step 2, the polyethylene film is rolled over in preparation for knurling and/or heat sealing. Knurling and/or heat sealing the polyethylene film forms a longitudinal seal along a length of the tampon wrapper as shown in Step 3. A tampon pledget and/or tampon applicator is/are inserted into the polyethylene film that has the longitudinal seal, as shown in Step 4. Opposite ends of the polyethylene film that is rolled over is sealed by knurling and/or heat sealing the pledget and/or tampon applicator inside of the tampon wrapper 10, as shown in Step 5. A notch and one or more perforations may be added, as shown in Step 6 by a cutting die, a cutting mechanism, or cutting mechanisms. The longitudinal seal is knurled at a temperature of about 80 degrees Celsius to 120 degrees Celsius. The end seals are knurled at a temperature of about 80 degrees Celsius to 120 degrees Celsius. The polyethylene film may have a melting point of 120 degrees Celsius.

Opposite ends of the polyethylene film that is rolled over may be sealed by knurling with one or two tip forming cassettes having a knurl pattern. Two tip forming cassettes may be used that have knurl patterns that are inverted to one another so that the knurl patterns may nest together when the two tip forming cassettes are pressed together. A tip forming cassette 100 that may be used to form seals on the opposite ends of the polyethylene film that is rolled over, is shown in FIGS. 6 through 9. The tip forming cassette 100 has a plurality of teeth 110. The teeth 110 may be straight or diagonal teeth (hills) or indentions (valleys) that resemble pyramids, cones, or other raised or recessed shapes. Each of teeth 110 may have a square shape bottom portion 112 with sides that are, preferably, about 1.5 millimeters to about 2.5 millimeters, and more preferably, about 2.00 millimeters, and that taper to a square shaped tip 113 having sides that are about 0.44 millimeters to about 0.64 millimeters, and more preferably, about 0.49 millimeters to about 0.59 millimeters. A height H from bottom portion 112 to square shaped tip 113, preferably, is about 0.20 millimeters to about 1.20 millimeters, and more preferably, about 0.70 millimeters. Each of teeth 110 may have a radius of curvature from a first side 115 side to a second side 120, preferably, equal to about 2.0 degrees to about 3.0 degrees, more preferably, about 2.5 degrees. The teeth 110 may have a radius of curvature from one protrusion tip 125 to another protrusion tip 130, preferably, equal to about 1.38 degrees to about 2.38 degrees, and more preferably, equal to about 1.84 degrees to about 1.88 degrees. The radius R may be about 43.15 millimeters. Preferably, teeth 110 have an angle A therebetween that is about 90 degrees.

While the instant disclosure has been described with reference to one or more exemplary embodiments, it will be understood by those skilled in the art that various changes may be made and equivalents may be substituted for elements thereof without departing from the scope thereof. In addition, many modifications may be made to adapt a particular situation or material to the teachings of the disclosure without departing from the scope thereof. Therefore, it is intended that the disclosure not be limited to the particular embodiment(s) disclosed as the best mode contemplated for carrying out this disclosure.

What is claimed is:

1. A method of making a tampon wrapper comprising:
   perforating a polyethylene film while in flat state;
   rolling said polyethylene film over to form a tube;
   knurling and/or heat sealing said tubular polyethylene film to form a longitudinal seal along a length of the tampon wrapper;
   sealing a first perforated end-seal of said tubular polyethylene film;
   punching a notch out of the first perforated end-seal;
   inserting a tampon pledget and/or tampon applicator into an open second end of said polyethylene film tube; and
   forming a second end-seal by knurling and/or heat sealing said open second end.

2. The method of claim 1, wherein said first perforated end-seal is knurled at a temperature of about 80 degrees Celsius to about 100 degrees Celsius.

3. A method of making a tampon wrapper comprising:
   notching and perforating a polyethylene film while in flat state;
   rolling said polyethylene film over to form a polyethylene film tube;
   knurling and/or heat sealing said tubular polyethylene film to form longitudinal seal along a length of the tampon wrapper;
   sealing a notch end-seal by knurling and/or heat sealing a first end of said polyethylene film tube;
   inserting a tampon pledget and/or a tampon applicator into an open second end of said polyethylene film tube; and
   forming a final end-seal by knurling and/or heat sealing said open second end.

4. The method of claim 3, wherein said notch end-seal is knurled at a temperature of about 80 degrees Celsius to about 100 degrees Celsius.

5. A method of making a tampon wrapper comprising:
   rolling a polyethylene film over to form a polyethylene film tube;
   knurling and/or heat sealing said tubular polyethylene film to form a longitudinal seal along a length of the tampon wrapper;
   inserting a tampon pledget and/or a tampon applicator into a first open end of said polyethylene film tube;
   forming a notch end-seal and a final end-seal by knurling and/or heat sealing said first open end and a second end of said polyethylene film tube; and
   adding a notch and one or more perforations, said plurality of perforations extending from said notch to a stop mechanism, said polyethylene tube forms a first portion, a second portion, and an open volume portion when the tampon wrapper is torn along said plurality of perforations up to said stop mechanism, and said first portion and said second portion being tieable to form a closed volume with a used tampon applicator and/or plunger within said open volume portion.

6. The method of claim 5, wherein said notch end-seal is knurled at a temperature of about 80 degrees Celsius to about 100 degrees Celsius.

7. The method of claim 5, wherein said first end and said second end of said polyethylene film tube are sealed by knurling with a tip forming cassette having a knurl pattern, wherein said tip forming cassette has a plurality of protrusions with each of said plurality of protrusions having a square shape bottom portion with sides that are about 2.00 millimeters that taper to a square shaped tip having sides that are about 0.49 millimeters to about 0.59 millimeters.

* * * * *